United States Patent
Larsen

(10) Patent No.: US 7,311,722 B2
(45) Date of Patent: Dec. 25, 2007

(54) PHOTODYNAMIC STIMULATION DEVICE AND METHODS

(76) Inventor: Eric Larsen, P.O. Box 1016, Schaffhausen (CH) CH-8201

( * ) Notice: Subject to any disclaimer, the term of this patent is extended or adjusted under 35 U.S.C. 154(b) by 135 days.

(21) Appl. No.: 10/466,734
(22) PCT Filed: Jan. 22, 2002
(86) PCT No.: PCT/NO02/00033
§ 371 (c)(1), (2), (4) Date: Jan. 12, 2004
(87) PCT Pub. No.: WO02/062420
PCT Pub. Date: Aug. 15, 2002

(65) Prior Publication Data
US 2005/0075703 A1  Apr. 7, 2005

(30) Foreign Application Priority Data
Jan. 22, 2001 (NO) .................................. 20010373

(51) Int. Cl.
A61N 5/06  (2006.01)
(52) U.S. Cl. .............................. 607/88; 128/898; 606/9
(58) Field of Classification Search .................... 606/9; 607/88–90; 128/898
See application file for complete search history.

(56) References Cited

U.S. PATENT DOCUMENTS

| | | | |
|---|---|---|---|
| 4,718,416 A | * | 1/1988 | Nanaumi ........................ 606/9 |
| 5,095,901 A | | 3/1992 | Davitashvili et al. |
| 5,207,671 A | * | 5/1993 | Franken et al. ................. 606/9 |
| 5,226,907 A | | 7/1993 | Tankovich |
| 5,304,207 A | | 4/1994 | Stromer |
| 5,662,644 A | * | 9/1997 | Swor .............................. 606/9 |

(Continued)

FOREIGN PATENT DOCUMENTS

EP  A-0320080  6/1989

(Continued)

OTHER PUBLICATIONS

Karu T., Pyabrat L., Kalendo G., Irradiation with He-Ne laser increases ATP level in cells cultivated in vitro. *J. Photobiol. B*. 1995; 27(3): 219-23.

(Continued)

*Primary Examiner*—Henry M Johnson, III
(74) *Attorney, Agent, or Firm*—Cohen Pontani Lieberman & Pavane LLP

(57) ABSTRACT

A treatment device which uses a light radiation of multiple wavelengths and pulse-shaped electromagnetic fields for the photodynamic stimulation of cells, especially cells of human tissue, and also for the activation and stimulation of light sensitive substances (PTD). The device produces energy radiation by the use of semiconductor and/or laser diodes, which emit light in several separate wavelengths due to a special operation mode and the use of tuneable diodes. The equipment consists of a stand, with which machine applicators are connected via a jointed arm. The stand is freely moveable on wheels and includes a control mechanism whereby the various parameters for therapy can be adjusted and switched on and off. The stand is also connected to a hand applicator for treatment of small tissue-areas, e.g., acupuncture points. Photodynamic substances are introduced into the tissue with a special hand applicator.

50 Claims, 6 Drawing Sheets

U.S. PATENT DOCUMENTS

| | | | | |
|---|---|---|---|---|
| 5,843,072 | A | * | 12/1998 | Furumoto et al. .............. 606/9 |
| 5,944,748 | A | * | 8/1999 | Mager et al. .................. 607/88 |
| 6,450,941 | B1 | * | 9/2002 | Larsen ......................... 600/14 |
| 6,616,946 | B1 | * | 9/2003 | Meier et al. ................. 424/489 |
| 6,663,659 | B2 | * | 12/2003 | McDaniel ..................... 607/88 |
| 6,758,845 | B1 | * | 7/2004 | Weckwerth et al. ............ 606/9 |
| 6,835,202 | B2 | * | 12/2004 | Harth et al. ................... 607/91 |
| 6,835,393 | B2 | * | 12/2004 | Hoffman et al. ............. 424/450 |
| 6,981,499 | B2 | * | 1/2006 | Anderson et al. ...... 128/200.23 |
| 2001/0007666 | A1 | * | 7/2001 | Hoffman et al. ............. 424/400 |
| 2003/0060810 | A1 | * | 3/2003 | Syrowicz et al. .............. 606/9 |
| 2005/0004631 | A1 | * | 1/2005 | Benedict ....................... 607/88 |
| 2005/0004632 | A1 | * | 1/2005 | Benedict ....................... 607/88 |
| 2005/0075703 | A1 | * | 4/2005 | Larsen ......................... 607/88 |

FOREIGN PATENT DOCUMENTS

EP           A-568666          11/1991

OTHER PUBLICATIONS

Lievens P., The influence of Laser-irradiation on the motricity of lymphatic system and the wound-healing process. The influence of low level infrared laser therapy on the regeneration of cartilage tissue. Univ. of Brussels/Dep. Of Rehabilitation: Int. Congress in med. and surgery, abstract, Bologna/www.Laser.nu.

Poentinen P., Airaksinen O., Ratanen P., Kolari P., Effects of infrared laser irradiation at the trigger points. *Kuopio Univ. Hospital*, Kuopio, Finland. *Published: SJA & ET*, 1988, 3/56-61.

Papageorgiou P., Katsambas A., Chu A., Phototherapy with blue (415 nm) and red (660 nm) light in the treatment of acne vulgaris. *J. Dermatol*. 2000, May; 142 (5); 973-8.

Itoh T., Murakami H., Oribashi K., Sueda T., Kusumoto Y., Kakehashi M., Matsuura Y.: Low power laser products human erythrocytes in an in vitro model of artificial heart-lung machines. *Artificial Organs*, 2000; 24 (11): 870-3.

Siposan G. Dan: An in vitro study of te effects of low-level laser radiation on human blood.

Bakeva L. E., Manteifel V. M., Rodichev E.B., Karu T.: Formation of gigantic mitochondria in human blood lymphocytes under the effect of a He-Ne Laser. *Mol. Biol.* (*Mosk.*) May-Jun.; 27 (3); 608-17.

Wolf P., Rieger E., Kerl H. (1993): Topical photodynamic therapy with endogenous prophyrins after application of 5-aminolevulinic acid an alternative treatmen modality for solar keratoses, superficial squamos cell carcinomas, and basal cell carcinomas. *J. Dermatol*. 28:17-21.

Okunaka T., Kato H.: Depart. of surgery, Tokyo Medical University, Japan: Photodynamic therapy for lung cancer: state of the art and expanded indication, *Int. laser Congress 2003*, Munich, Jun. 25-27, Abstract/Medline.

Waidelich R., Beyer W., Knuchel R., Stepp H., Baumgartner R., Schroder J., Hofstetter A. Kriegmair M: Dept. of urology, University of Munich: Whole bladder photodynamic therapy with 5-aminolevulinic acid using a white light source., *Int. Laser Congress 2003*, Munich, Jun. 25-27, Abstract.

\* cited by examiner

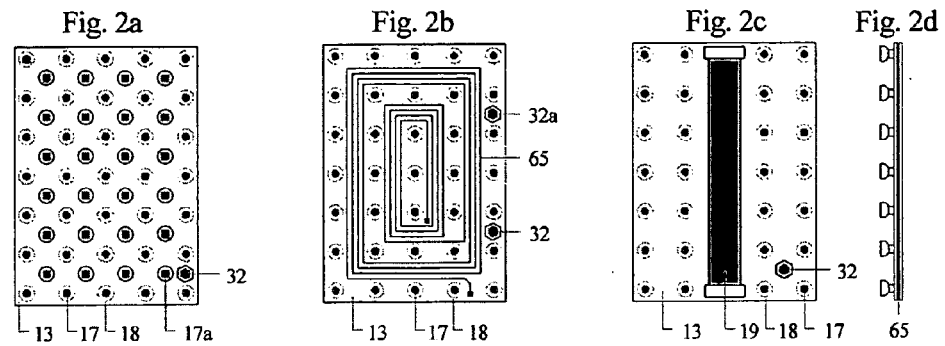
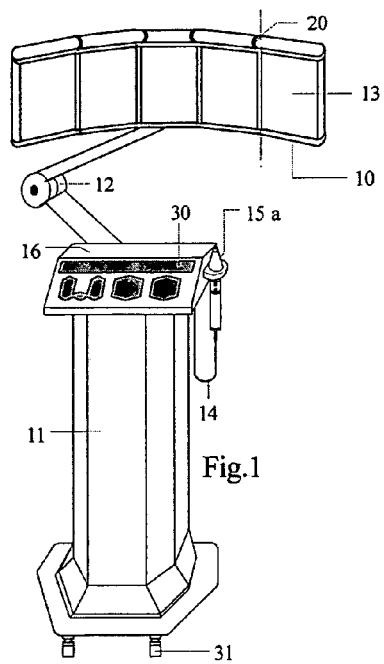
Fig.1
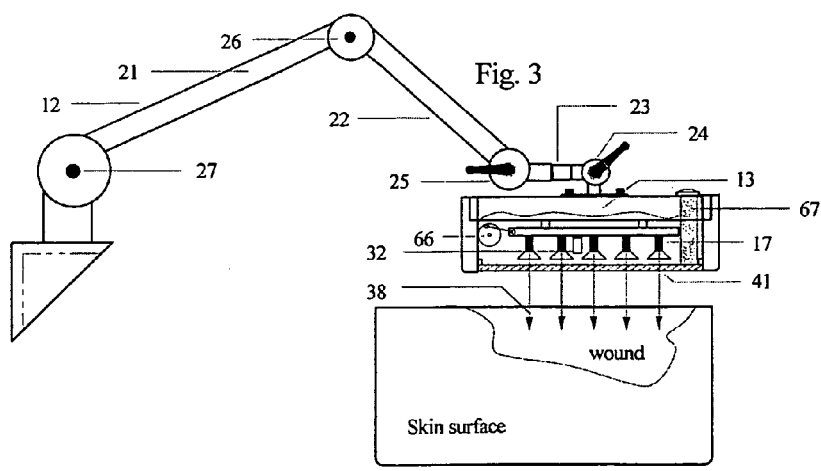
Fig. 3

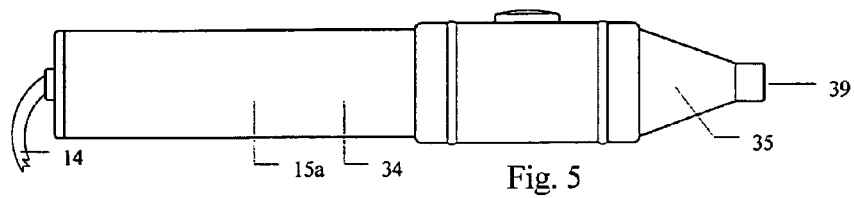
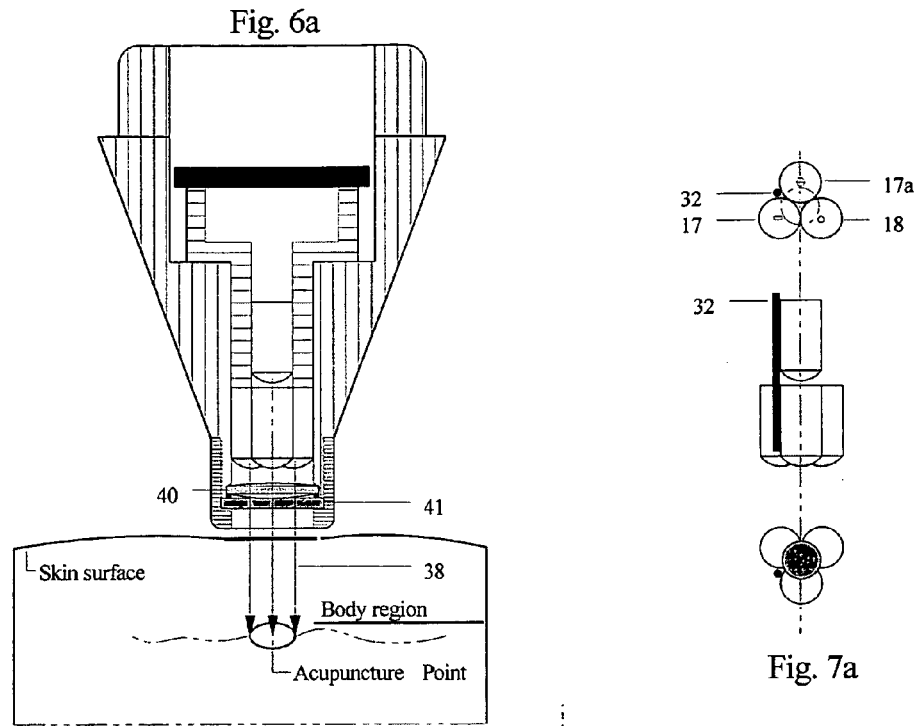
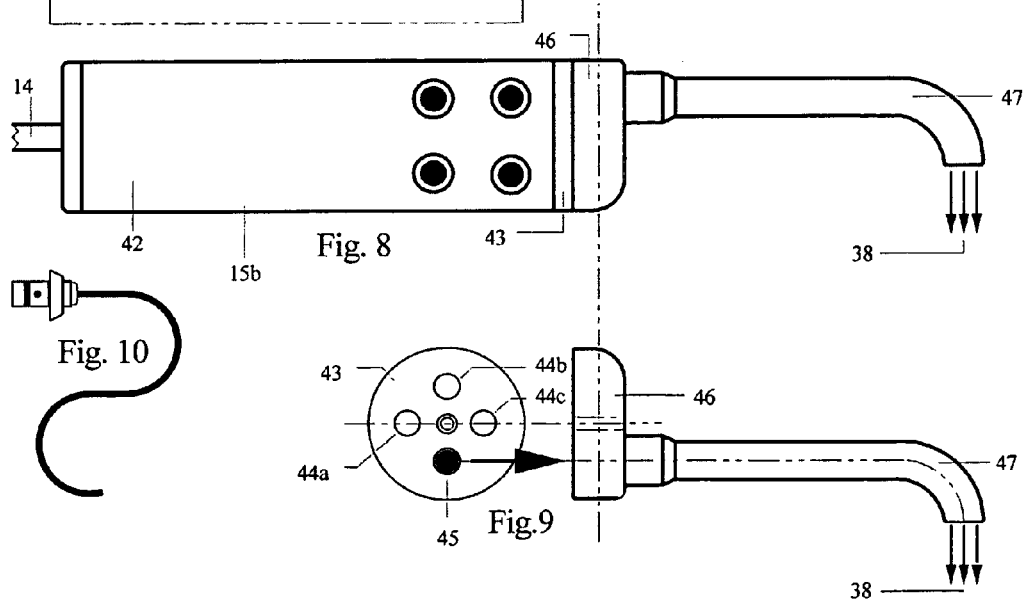

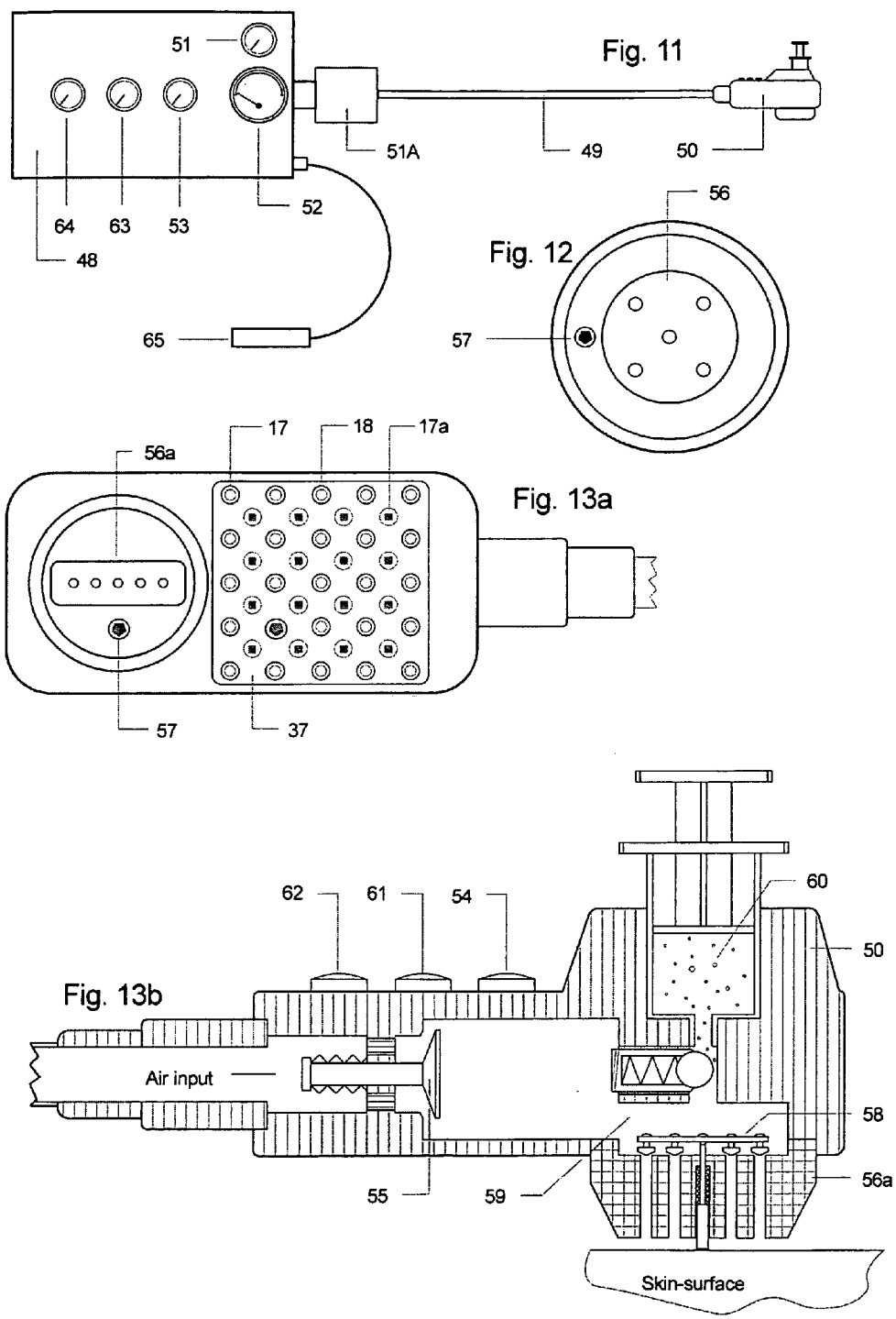

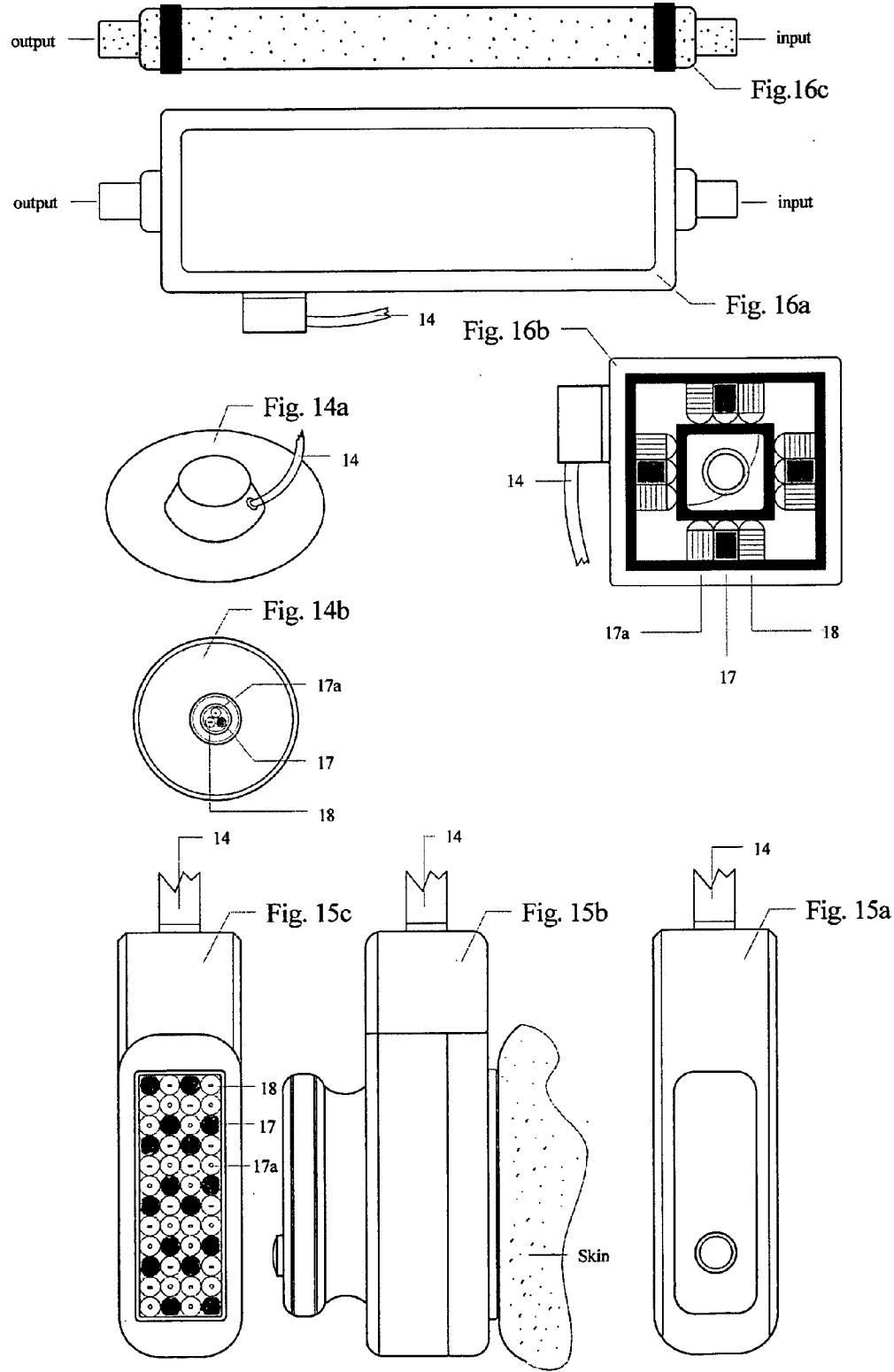

PHOTODYNAMIC STIMULATION DEVICE AND METHODS

PRIORITY CLAIM

This is a U.S. national stage of application No. PCT/NO02/00033, filed on Jan. 22, 2002. Priority is claimed on that application and on the following application(s): Country: Norway, Application No.: 20010373, Filed: Jan. 22, 2001.

BACKGROUND OF THE INVENTION

1. Field of the Invention

The present invention relates in general to electrotherapy devices and more particularly to devices and methods for photodynamic and electromagnetic stimulation of living tissue, directly and also indirectly, by stimulation of photosensitive substances introduced into or onto living tissue.

2. Description of Related Science

The mitochondria within the cells of protozoa and metazoa are sources of energy produced by cell respiration. They are moreover capable of synthesizing proteins, because they have a genetic system of DNA and RNA independent of the cell nucleus.

The mitochondrias' main function, however, is vesicular respiration. This is the transformation within the cells of nutrients and oxygen (supplied, amongst other ways, via the bloodstream) into energy and endogenous substances, whereby through this transformation, waste products like water, carbon dioxide, alcohol and lactic acid are produced. Of great importance is adenosine-triphosphoric acid (ATP), which is synthesized by the mitochondria into adenosine-diphosphoric acid (ADP) and orthophosphate. Complicated chemical compounds are of great importance as reaction catalysts.

Stimulation of the vesicular respiration, especially a stimulation of the ATP production by cells, is used therapeutically to meet strong demands on cell energy during healing processes, and for weight-reduction, wound-healing and reduction of pain sensitivity due to illness or weakness caused by hypo- or depolarization of the cell membrane. In general, weakening of cells caused by an increase of vesicular respiration due to stress, illness or by old age can be counteracted. In order to achieve stimulation of the mitochondria through optical radiation, two conditions must be fulfilled. The radiation must be of appropriate wavelengths in order to be effective, and a pulse frequency must be chosen to penetrate to an appropriate tissue depth without causing tissue damage or pain.

Moreover, pulsating electromagnetic fields have been shown to exert a positive influence on the bodies of both animals and humans. With the help of pulsating electromagnetic fields it is possible to send protons from electrolytic internal body fluids such as blood or lymph directly and in controlled measures into the surrounding vessel walls and membranes. This is normally not possible, since the lipids in the membranes of the blood vessel walls, which are in contact with the blood, carry a negative charge creating a surface potential which hinders the protons and ions from entering the vessel walls. The pulsating electromagnetic field enables the protons to enter the cell and vessel walls in spite of the barrier. When this occurs, the increased concentration of protons in the cell and vessel walls reverses the polarity of the barrier, thereby hindering the protons and ions from exiting through the cell and vessel walls again. In turn, this phenomenon causes a beneficial change in the local pH value, especially within the vessel walls. Additionally, prolonged exposure to pulsating electromagnetic fields has other effects, such as the electrical constriction of the membranes and vessel walls, the adjustment of polyvalent ion chains, the tangential displacement of absorbed counter ions, the force effect on dielectric bodies in homogeneous and non-homogenous fields, and electro-osmosis.

A device is known (Patent DE-U-8-13852/Normed, E. Larsen). which uses infrared radiation for the photodynamic stimulation of energy in living cells, cells at the surface of the skin and especially cells lying deeper down. The device consists of a supply and control mechanism and an applicator on which infrared radiating (from 900 nm [1 nm=1 nanometer]) semiconductor diodes are mounted with reflectors for the bundling of the IR radiation from the applicator (IR=infrared). In this known device, a generator containing a control-mechanism supplies the semiconductor diodes with current pulses of a frequency within the range of 500-5000 Hz. A disadvantage of the known device is that the semiconductor diodes tend to overheat during use, which causes a decrease in the effectiveness of the device.

The known device therefore does not deliver a constant effect during use. Another disadvantage is that only infrared radiation within a range of 900 nm is available, while other wavelengths may be called for to achieve cell stimulation.

Another device (Patent EPA 0568 666) is used for the photodynamic stimulation of cells. The semiconductor and/or laser diodes radiate light of different wavelengths. With the aid of light sensors the advanced control-system is able to test the patients for the required radiation dose in order to avoid over-stimulation. Furthermore, the radiation outlets in the applicators are covered with a polarization filter, which enhances absorption in the irradiated tissue. The basic equipment consists of a mobile stand, to which machine applicators are connected with a jointed arm. The machine applicators are adapted for the treatment of large tissue-areas, for example the back of humans. The device also includes a control-mechanism, whereby the various parameters for therapy can be adjusted and switched ON and OFF. The device is also connected to a hand applicator designed for the treatment of small tissue-areas, e.g. acupuncture points or dental treatment with the aid of a connectable fibre.

Another device is (EPA Patent 0570 544), which uses electromagnetic fields for therapy on humans and animals. The pulse-shaped electromagnetic fields cause protons to migrate out of the electrolytic internal body fluids into the surrounding vessel walls and membranes. The device produces the electromagnetic pulse-bundles in a certain pulse-rhythm, in which each pulse-bundle is followed by a pause. The basic device consists of a generator for producing the electro-magnetic pulses, connected with a transmitter coil, whose windings are placed on the surface of the base plate. The base plates are manufactured from light, flexible insulating material and mounted in a flat applicator housing placed on a jointed arm connected to the basic device.

In the fields of dermatology and rehabilitation, light is used as a stand-alone therapy for wounds, leg ulcers, eczema, burns, pain, rheumatic disorders etc., and as such is used to stimulate tissue directly. Techniques are known for introducing agents for altering the light absorbing qualities of tissue to enhance the effect of light (for example, U.S. Pat. No. 5,226,907 to Tankovich teaches contamination of hair follicles with a dark particulate material to enhance light-induced heating in the follicles for hair removal).

Treatments have included the application of substances such as photoflim, 5-aminolevulan acid, hematoporphyrin, verteporfin, chlorins, phthalodyanines, phenothiazine, and benzoporphyrin-derivative monoacid-A (ATMPn) onto or into tissue for healing solar keratoses, basal cell carcinoma, melanomas, etc. Such substances are known as "biopharmaceuticals" and treatment with these substances has been called biopharmaceutical therapy. Therapy involving the application of biopharmaceuticals and their subsequent activation by light after they have been absorbed into tissue has been called photodynamic therapy (PDT).

PDT has been used successfully in the treatment of internal inoperable cancers. A biopharmaceutical (specifically, hematoporphyrin) is injected into the tumor tissue, and an optical method known as photodynamic diagnosis (PD) is used to determine when the biopharmaceutical has been absorbed by the entire tumor. Then the tumor tissue is irradiated with light typical for a dye laser, which activates the photosensitive reactors in the hematoporphyrin, whereby singlet oxygen is liberated. Singlet oxygen is toxic to protein and phosphorlipids in the tumor tissue, whereby the tumor is destroyed without destroying the surrounding tissue.

For treatment of skin keratosis (pre-cancerous tissue), trials with, for example, 5-aminolevulinic acid have shown that it can be used effectively in PDT if introduced into oil in a water suspension which is then applied to skin keratosis and then irradiated with a light source. A fast and cosmetically perfect healing has been attained with a very low rate of recurrence compared to conventional treatments, such as cryo-therapy. In view of these favourable test results, it is anticipated that pharmaceutical companies will be marketing the next generations of PDT chemicals in convenient forms, such as creams, suspensions, sprays, etc.

The light source typically used to irradiate PDT chemicals is commonly known as the surgical laser, a solid-state laser which is bulky, and which is expensive both to purchase and to operate. Surgical lasers are designed primarily for cutting, i.e., they output very high energy in a very small spot, and are thus difficult to adapt to the requirements of irradiating a more generalized area for PDT. Further, they generally radiate at a single wavelength Radiation at several wavelengths is desirable in PDT, for several reasons: a single wavelength may cause the patient to experience burning pain in adjacent tissue during treatment; some photosensitive chemicals respond to two different wavelengths; and, some pigmented melanomas do not respond to visible radiation due to absorption in the pigment (typically melanin), and must be irradiated with near-infrared light.

Common dermatological diseases like acne, warts, and onychomycosis (nail fungus) can successfully be treated with light as a stand-alone treatment, but recent work indicates that treatments using PDT (with ALA/5-aminolevulanic acid) give excellent results with only two or three treatments.

In a recent pilot study using PDT to treat acne, the cosmetic results were excellent, and oil gland activity which causes acne, and the resultant inflammation, were reduced for as much as twenty weeks after a series of PDT treatments. (The PDT treatments precipitated immediate but short-term inflammatory reactions.) In general the photodynamic stimulation used in physiotherapy is producing very good results, but in the area of long-term chronic diseases such as gout, arthritis, etc. there is often a need for many treatments, as many as 12-20 treatments spaced over a period of time. Also, initial phases of such treatment often cause reactions, which in turn cause pain and discomfort. A recent trial study showed that using a light and/or laser radiation combined with an electromagnetic field emission resulted in better results, without reactions to the intensive therapy. It seems that the combined radiation has a better penetration due to the electromagnetic fields removing the blocking potential and the vasodilatation of the capillaries, whereby the increased ATP energy is better utilized.

A recent trial in post-surgery light and/or laser therapy after coronary angioplasty and stenting, where the restenosis rate is normally quite high, showed promising results, and here again it is expected that the results can be improved using a light sensitive biopharmaceutical for regeneration and stabilisation of the vessel walls.

Studies also support the theory that a light and/or laser radiation of blood can provide an effective therapy for chronic diseases such as leukemia and cancer, our tests on athletes also support the theory that this therapy improves the immune system and the vitality.

A number of erothrocytes are often damaged in artificial heart-lung machines, but blood irradiated with light and/or laser showed less deformability and the ATP levels were significantly higher. Here too we expect an increased activity of the leukocytes and and lymfocytes by using light sensitive biopharmaceuticals.

For many years large-surface therapy systems for dermatological diseases like psoriasis have been equipped with UV radiation sources, for example UV tubes. Prior to the treatment the patients have received various types of photochemical substances like 8-MOP (Oxsoralen), 5-MOP or Meladinine (bathing therapy). Due to the risk of skin cancer and other side effects the use of PUVA therapy has declined during recent years. When more studies have been completed it is expected that PDT will in future be the procedure of choice for treating most chronic dermatological diseases, due to its effectiveness and lack of side effects.

Also due to the risk of skin cancer, tanning on sun-beds has declined much during recent years. Among other side effects is the erythema that follows the first treatments, and most patients, especially those with fair skin, find that their skin becomes very dry and irritated.

Our tests have showed that by using a combination of UV light and photodynamic light produced by semiconductor diodes, we can avoid all the side effects of using sun-beds. It is also expected that the increased vitality (high ATP level) of the skin can counteract the risk of skin cancer.

In classical acupuncture a technique called moxibustion is commonly used for the treatment of deep-lying acupuncture points, especially in chronic diseases. Needles with a special metal handle are used and, after the needles are inserted in the patient, a herbal substance is placed on the handle and combusted, whereby the needle is heated and leads the heat deep into the tissues. The effect is excellent, but western doctors do not like this praxis because of the strong smell, which may linger for several days.

This method can now be replaced by the application of topical light-sensitive lotions over the acupuncture points, which are subsequently radiated with a suitable light and/or laser radiation. Looking at the current state of technology, devices are available for the photodynamic stimulation of human cell energy in the form of red and infrared radiation emitted by laser diodes and semiconductor diodes. These devices are not suitable for intensive, invasive and whole body treatments mainly due to the lack of applicators with suitable adjustable radiation sources for fill surface treatment with combined diagnostic abilities during treatment. The same can be said for existing devices for treatment with pulsating electromagnetic fields. Moreover, a combined treatment with both red/infrared and blue light together with electromagnetic fields is not possible with these devices for the stimulation of light sensitive substances.

A device able to deliver an intensive light radiation with selective multiple wavelengths within the wavelength area of 300-2000 nm and electromagnetic fields is not at present available. Thus the invention is aimed at creating a device for intensive photodynamic therapy, which is capable of stimulating photodynamic energy of selective multiple light and/or laser radiation within a wavelength range of 300-2000 nanometers, capable of treatment with pulsating electromagnetic fields, and can also be used for stimulating light sensitive biopharmaceuticals.

SUMMARY OF THE INVENTION

The present invention provides a device with changeable applicators using a light and/or laser radiation of several wavelength ranges suited for the photodynamic stimulation of the cell energy in living cells, in particular human cells of both surface and underlying tissue. The light and/or laser radiation especially enhances vesicular respiration, most particularly stimulation of the ATP production in cells, thus increasing the therapeutic capabilities of the device. Furthermore, it is also possible to stimulate the activity of the cytochromes and the enzyme activity of the cells.

The device consists of a stand, to which machine applicators are connected by means of a jointed arm. The stand, freely moveable on wheels, consists of a control mechanism, on which the desired therapy data can be adjusted and the device can be switched ON and OFF. The plain surface applicators can consist of several applicators placed side by side and flexibly connected with each other through hinges, whereby the applicators are suitable for the treatment of large-area tissues such as the human back.

The applicators contain printed circuit boards mounted with semiconductor diodes and/or laser diodes (in large numbers), and the diodes are mounted with reflectors, which collect the radiation and bundle them in front of the applicator. The applicators also contain one or more transmitter coils for the emission of pulse-shaped electromagnetic radiation. The applicators are also equipped with an adjustable scan system, which permits an even and gap-free radiation of the surface with the multiple wavelengths of light.

A diagnostic system (PD) containing a fluorescent light source and optics for photodiagnosis during the treatment is also included in the applicator.

At least one of the applicator elements is equipped with feedback sensors for controlling the patient's response to the therapy, and via an automatic regulation system in the control mechanism it is possible to optimise the therapy results. The applicator contains a polarization filter, which is placed directly in front of the diodes. The control mechanism is also connected with a hand applicator, which is constructed for treatment of small tissue areas, e.g. acupuncture points and trigger points (pain points).

The hand applicator includes a cylindrical shaft to which a headpiece is connected. A printed circuit board is fastened to the headpiece, mounted with semiconductor diodes or laser diodes. The light radiation is emitted from an axial opening in the front, equipped with a polarization filter and a lens for the focusing of the light rays.

A second version hand applicator, which is especially invented for dental and/or invasive treatment, including (PD) diagnosis, contains at the front end of its shaft a printed circuit board, where 4 light and/or laser diodes of different wavelengths are placed at 90° intervals. One of these radiation sources can be selected as a fluorescent light for diagnostic purposes (PD) related to PDT therapy using light reactive biopharmaceuticals. The headpiece in front of the printed circuit board can be rotated in steps of 90° so that the expander, which is connectable with various types of optical fibres, can be positioned in front of either radiation source. The applicator may selectively emit blue light for the bonding and hardening of composite plastic fillings or infrared light for the treatment of dental pain, gingivitis, and wounds. In order to optimise bonding with the blue light, the output of the hand applicator is supplied at 25% of full power for the first ten seconds of the radiation time, and then is switched to full power.

Acupuncture applicators made as small heads mounted on self-adhesive pads connected to the control mechanism, allow a certain number of applicators to be connected corresponding with the usual number of points utilised in classical acupuncture. The control mechanism can be programmed for a randomised acupuncture programme with changing frequency, modulation and amplitude instead of a programme with classical needling and Moxa treatment.

Two applicator types are made for the stimulation of blood, either of venous blood or integrated in a heart/lung-machine. The first applicator allows radiation of blood passing the applicators' radiation sources in a 5 mm infusion lead, and the second version provides an intensive radiation of a quadrant tube, where the blood passes and receives radiation from 4 sides from light and/or laser diodes mounted on print-boards also containing transmitter coils radiating pulse-shaped electromagnetic emission.

The applicators can also be designed as standard 2 meter and 15 cm long light tubes of the type commonly used in sun-beds for whole body therapy. Here it is advantageous to make the applicator in the form of a flat oval tube in order to achieve a better radiation surface. The tube applicators contain print-boards mounted with a suitable number of semiconductor light and/or laser-diodes as well as transmitter coils for the emission of pulse-shaped electromagnetic fields. The applicators are then mounted in a large body treatment arrangement like a sun-bed, where the patient lies on the lower part beneath a top part covering the whole body. Applicators of this type could be useful for treating office workers suffering from SAD disorders caused by too little exposure to natural light.

The invention provides multiple wavelength stimulation that is also effective in conjunction with photodynamic therapy (PDT) chemicals. Such chemicals are applied or injected into or onto tissue to be treated, and subsequent photo-stimulation of them causes reactions in them that result in treatment of the tissue. Irradiation at multiple wavelengths enhances the effects of PDT chemicals while reducing discomfort to the patient.

The present invention provides an apparatus including a semiconductor light source including a hand applicator. The hand applicator can selectively emit light of various wavelengths and introduce the light-sensitive substances into the tissue by means of air-pressure and electrical impulses (iontophoresis). The absorption time, depending on the type of light-reactive substances, may vary from 1 to 24 hours without this technique. Other advantages with the described technique are that the light-sensitive substances can be applied very precisely and the absorption dose can be improved and more accurately regulated.

Other advantages of the invention will become evident from the following description of the invention and from the appended drawings, wherein:

BRIEF DESCRIPTION OF THE DRAWINGS

FIG. 1 is a perspective drawing of the invented device,

FIGS. 2a, 2b, 2c, 2d illustrate details of the machine applicator of the invented device;

FIG. 3 illustrates a jointed arm used for the movable connection of the machine applicators;

FIG. 4 is a circuit block diagram of a control unit, which supplies the applicators.

FIG. 5 depicts a hand applicator according to the present invention;

FIG. 6a depicts a cross section of the hand applicator of FIG. 5;

FIG. 7a depicts a cross-section of the light sources of the hand applicator of FIG. 5;

FIG. 8 an applicator with a rotary headpiece;

FIG. 9. shows details of a printed circuit board for the applicator of FIG. 8; and FIG. 10 depicts the flexible light fibre cable with adaptor, FIG. 11 shows the air unit with the hand applicator belonging to this part of the invention.

FIG. 12 illustrates an exchangeable round head for the hand applicator.

FIG. 13a shows the hand applicator for light-sensitive substances viewed from below.

FIG. 13b illustrates the hand applicator in side view.

FIG. 14a shows the acupuncture applicator in top view,

FIG. 14b depicts the acupuncture applicator from the underside, showing the light sources.

FIG. 15a illustrates a rectangular hand-applicator in a top view;

FIG. 15b shows the hand applicator in side view with skin contact used for hair removal;

FIG. 15c illustrates the hand applicator viewed from below, showing the light sources;

FIG. 16a illustrates a tube applicator for the radiation of blood;

FIG. 16b shows the applicator-like quadratic tube viewed from the end;

FIG. 16c shows the quadratic tube used for blood radiation;

FIG. 17c illustrates the closed body applicator in a side view.

DETAILED DESCRIPTION OF THE PREFERRED EMBODIMENT

Figure 7:
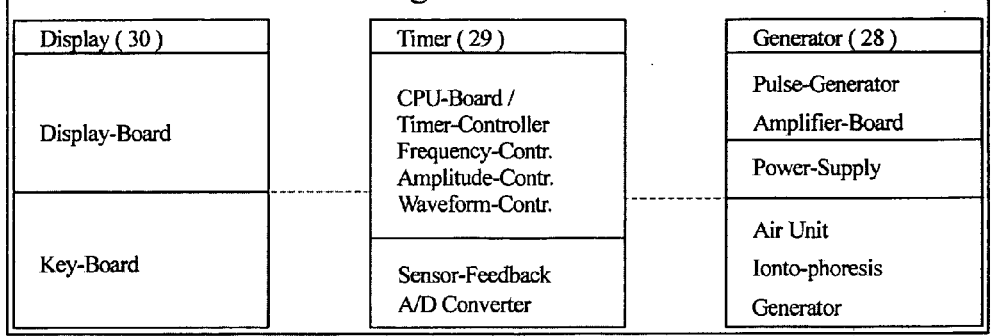
FIG. 7 depicts a schematic representation of the light sources with a sensor of FIG. 6.
Figure 6:
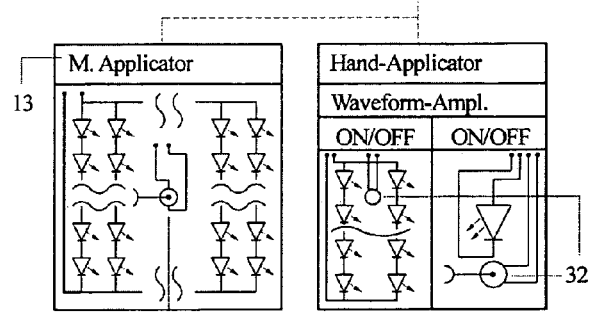
FIG. 6 depicts a schematic representation of an applicator conforming to FIG. 5 with axial light emission.

As shown in FIG. 1, the invented device 10 for the stimulation of cells with the aid of (PDT) photodynamic light and electromagnetic fields combined with light sensitive substances consists of a stand 11, with which machine applicators 13 (in the following just called applicators 13) are connected through a jointed arm 12. The stand 11 is also connected by an electric circuit 14 with a hand applicator 15. The stand 11, freely movable on wheels, includes control mechanism 16 (described in FIG. 4), whereby the function of the control mechanism 16 can be adjusted and switched ON/OFF at a control panel 30 (also called description equipment 30).

The FIGS. 2a, 2b and 2c show plain surfaced printed circuit boards with light sources mounted in the applicators 13. These can be used in the working model according to FIG. 2a to 2c individually, side by side (in large numbers) or in combination with an applicator. Furthermore the printed circuit boards on which the light sources are mounted can favourably be produced as multilayer, also containing the electromagnetic field transmitter coils 65 shown in FIG. 2d. According to FIG. 2a, the applicators 13 in the working model are mounted in a shifting order with semiconductor diodes (LED) and/or laser diodes 17 and 17a Cm the following called light sources), whereby shifting the order of the light sources 17 means, that the respective light source 17a of one row is placed at the point of intersection of the two diagonals through the two respective light sources 17, which are placed adjoining on both sides. The light sources 17 and 17a are mounted with reflectors 18, which collect the radiation and bundle it in front of the applicator 13. The applicator contains a polarization filter, which is placed directly in front of the light sources 17 and 17a, whereby the radiation can be better absorbed by the irradiated tissue.

According to FIGS. 2b and 2c the light sources 17 are placed in regular row arrangements, i.e., 20 equidistant from each other, whereby, according to FIG. 2c, one applicator 13, in addition to the diodes 17, has a light source 19. The light sources 17 are adjustable and can radiate light in at least three wavelengths within the wavelength area 300-2000 nm. The light source 19 formed as a tube can be selected for radiating blue light or fluorescent light within the wavelength area of 300-450 nm for photodiagnostics (PD). A diagnostic system (PD) containing optics 67 with a magnifier for photodiagnosis during the the treatment is also included in the applicator. The light sources 17a (FIG. 2a) radiate light with a wavelength of 350-500 nm, i.e., blue light.

For the treatment of large-area tissues according to FIG. 1, several applicators 13 are flexibly connected to each other through hinges 10, respectively connecting one edge with the other, whereby the applicators are suitable for the treatment of for example, the backs of humans and so become adjustable for an equidistant positioning of the applicators 13 above the skin. In each applicator the printed circuit board carrying the light sources is connected to a small electrical scan engine 66, which can move the light sources with linear movements, whereby a correctly adjusted scan length and frequency gives the radiated surface a total radiation at the necessary wavelengths without leaving any unradiated gaps.

The jointed arm 12, shown in FIG. 3, connects one or more applicator(s) 13 with the stand 11. The jointed arm 12 has three joint carriers 21,22,23, where the joint carrier 21, together with the stand 11 and the joint carrier 23 are moveable at a free end through a fixing joint 24 connected with one or more applicators 13. Another fixing joint 25 connects the joint carrier 23 with 21, while the joint carrier 22 is connected with the joint carrier 21 with a hinge 26. The joint carrier 21 is connected with the stand 11 through a joint 27 and one or more joints can also be produced as friction-adjustable ball-joints, which gives almost unlimited adjustment possibilities and user comfort. The jointed arm 12 thereby allows the positioning of the applicators 13 in front of, or above, a tissue area while maintaining a correct positioning distance. The jointed arm 12 also carries the electrical circuits 14 (not further described) from the control mechanism 16, which is integrated in stand 11, to the applicator(s) 13.

According to FIG. 4 the controller mechanism 16 consists of a generator 28, a timer 29, and a display 30. With help of the generator 28 the current pulses necessary to the production of light and the current pulses for the supply to the transmitter coils emitting the electromagnetic fields are contributed, while with the aid of timer 29, all time functions are adjustable, e.g. the duration of treatment. Display 30 shows pertinent treatment data, such as current pulse frequency, pulse length, pulse amplitude and pulse modulation. With the help of the control mechanism 16, the invented device is adjustable within a relatively large range with reference to duration, amplitude and frequency of surge of current, so that the light sources, such as semiconductor diodes or laser diodes can be used.

For that purpose the control mechanism is equipped with a switch select system for operating different types of light sources 17, 17a, i.e. semiconductor diodes and/or laser diodes. Both semiconductor diodes and/or laser diodes with tuneable wavelengths can be operated, which is a great advantage, and therefore the printed circuit boards can be equipped with a more intensive radiation effect.

The semiconductor diodes and laser diodes are tuneable in wavelength by means of various methods such as resonators, piezo elements or by the help of special current modes.

The semiconductor diodes and/or laser diodes useable in this invention emit a light radiation with either SPE (single photon emission), TPE (Two photon emission) and/or MTE (multiple photon emission) within the wavelength area of 300-2000 nanometers in order to correspond with available light sensitive substances (PDT).

The useable light sources in the form of semiconductor diodes and/or laser diodes are supplied with current pulse lengths of ms, ns and/or fs (femto-seconds) within a frequency range of 1 KHz-100 MHz.

The transmitter coil (transducer) for transmitting the pulse-shaped electromagnetic fields is supplied with basic pulses having a frequency between 2 and 500 Hz; ON times of about four-tenths of a period; OFF times of about six-tenths of a period and non-instantaneous rise and fill times. Furthermore, the basic pulses can be superimposed with pulse-bundles at a frequency off about 10 KHz and, optionally, also with pulse-bundles of a frequency between 20-30 MHz.

The applicators 13, according to the FIGS. 2a, 2b and 2c are equipped with sensors 32 arranged between the semiconductor and/or laser diodes 17. For therapeutic uses it is typically intended to apply a given amount of energy (Joule/cm2) per irradiated surface of tissue, which can be adjusted at the control mechanism 16. Sensors 32 measure the amount of energy radiated away from the skin surface, which is indicative of the total energy penetrating into the tissue. Taking into account individual variations from patient to patient, the exposure can be determined according to the measurements taken by the sensors 32 so that the correct amount of therapeutic energy (Joule/cm2) reaches the tissue. An increase of the registered amount of energy can be achieved by the invented device by increasing the operating potential (and thereby the pulse amplitude) or the pulse frequency and/or prolonging the duration of the treatment time through an adjustment of the control mechanism 16.

A sensor 32a is also contained in at least one of the machine applicators, measuring the temperature change of the radiated tissue, whereby the control unit can react with a feedback regulation of the radiation parameters depending on the therapy indication, location and (PDT) light sensitive substance used.

While the applicators 13 according to FIGS. 2a, 2b and 2c are constructed for the treatment of larger tissue areas, the hand applicators 15a, 15b according to FIGS. 5 and 8 are constructed for the treatment of small tissue areas.

The hand applicator 15a includes a cylindrical shaft 34, with a handle to which a headpiece 35 is connected. At the headpiece 35 a printed circuit board 36 is fastened with light sources 17 of tuneable wavelengths (not described). In headpiece 35, in front of the opening 39, are placed a lens 40 for the focusing of the light rays and a polarization filter 41. The device with this kind of light 38 emission is especially designed for the treatment of small tissue areas, e.g. acupuncture points and triggerpoints.

FIG. 8, in connection with FIG. 9, describes a hand applicator 15b, which is especially intended for dental treatment and internal medical treatment. The applicator 15b shows at the front end of the shaft 42 a printed circuit board 43, where three different light sources 44 with tuneable wavelengths within the wavelength area of 300-2000 nm and a light source 45 for photodiagnostics (PD) are placed. In front of the printed circuit board 43 a headpiece 46 is placed, connected with an interchangeable fastened hollow expander 47, in which an optical fibre is sealed (not shown). The head piece 46 is in front of the printed circuit board 43 so it can be rotated 360° in steps of 90°, so that the expander 47 can be positioned in front of either one of the three light sources 44a, 44b, 44c, depending on the required wavelength for therapy, or in front of the light source 45 if fluorescent light for photodiagnostics (PD) is needed. If the expander 47 is positioned, for example, in front of the diode 44b, light within the infrared wavelength area is transmitted through the optical fibre in expander 47 and ultimately strikes the tissue, e.g. gum tissue, through which painful gingival diseases can be treated. Through a positioning of the expander 47 in front of the 44a, blue light with a wavelength of 470 nm is conducted through the expander 47, with which plastic fillings in teeth can be hardened. It is obvious that the light rays with this form of execution can also be conducted through polarization fibres. Furthermore, the two hand applicators are equipped with sensors 32 for the same purpose as described for the applicators 13. The hand applicator 15b can also be very useful in the case of internal medical diseases, where the flexible fibre cable can be used together with a video-cable, which is produced with an internal opening for instrumentation, laser fibre etc. In this situation the flexible light fibre cable is connected, whereby first the light source 45 is used for photodiagnosis and hereafter one of the light sources 44a, 44b, 44c is selected for the treatment.

FIG. 11 Shows a diagram of the air-pressure unit 48, which can either be built into the control mechanism of the device or produced as a separate device connectable with the invented photodynamic stimulation device. The air unit can either be produced as a rechargeable air-tank or as a small air-compressor with container. The container outlet is equipped with a reduction valve 51, combined with a pressure meter 52, of familiar sort. The electronic valve 51a in the air tube 49 leading to the hand applicator 50 can be switched on from the hand applicator and the ON impulses can be regulated at the control mechanism 53. The current impulses 63 and amplitude 64 for the iontophoresis treatment are also adjustable at the control mechanism.

FIG. 12 illustrates an interchangeable round head 56 for the hand applicator, which can be changed via a click in bracket (not illustrated). The treatment head 56 is interchangeable according to the purpose of radiation, so that a round head could be used for treating round spots, while a rectangular head 56*a* would be preferable for treating wrinkles.

In FIG. 13*a* the hand applicator is illustrated seen from below, mounted with a rectangular treatment head 56*a*. Next to the treatment head the light sources 17, 17*a* are placed in rows covered by a polarization filter 37 and/or lens system. A sensor 32 for feedback measurement is also integrated.

FIG. 13*b* shows a drawing of the hand applicator 50, which can be used for the following purposes:

Introducing light-reactive substances to the tissue with the aid of air-pressure pulses Introducing light-reactive substances to the tissue with the aid of iontophoresis Radiating the tissue with a mixture of light radiation, which can be selected on the control mechanism.

The hand applicator contains a valve 55 placed just after the air inlet, prohibiting the substances from running back into the air tube 49. The treatment head is mounted with a sensor 57 permitting exposure only on skin contact and furthermore the head also contains a valve-system 58, which opens only on skin contact, thus preventing the substances from running out of the head before it touches the skin.

The chamber 59 containing the substances is placed next to the air duct in the hand applicator 50 and the chamber is connected with a dosage pump 60, so that the amount of substance per air-shot can be dosed very accurately.

The hand applicator 50 housing is made of an insulating material, and the treatment head 56 is made of an electrically conductive material so that it can also be used for iontophoresis treatment combined with air-pressure treatment in order to attain maximum absorption.

Around the treatment head the light sources 17, 17*a*, are placed for the selective light radiation.

The ON/OFF switches 54, 61, 62 for operating the hand applicator are placed on the top of the applicator. During the iontophoresis treatment the patient must hold an electric conductor 65 handle in his hand.

FIG. 14*a* illustrates an acupuncture applicator made with a small head containing the light sources mounted on a self-adhesive pad connected to the control mechanism, which allows a certain number of applicators to be connected corresponding with the usual number of needles used in a classical acupuncture treatment. FIG. 14*b* shows the acupuncture applicator from the radiation side and the lens placed in this version over the light sources 17, 17*a*. The control mechanism can be programmed for a randomised acupuncture programme with changing frequency, modulation and amplitude. This method can easily replace the well-known Moxa method; Western doctors do not like Moxa treatment because of the smell it produces, although it is very effective for treating chronic diseases.

This form of light acupuncture is without any risk of infection as no needles are used. It is completely pain free and the benefit can be greatly augmented by applying a topical light sensitive lotion before radiation (PDT). The radiation of trigger points and/or acupuncture points with strong light sources can cause pain, but by choosing low frequencies and intensities in the start phase and successively increasing the frequency and intensity, the treatment is pain free and more efficient.

FIG. 15*a* shows a rectangular hand applicator with start-stop switch connected to the control mechanism with a cable. FIG. 15*b* shows an illustration of the hand applicator in side view, where the upper part is formed as a handle and the lower part is rounded for application directly onto the tissue to be treated, for example hair removal after application of light sensitive substances (PDT-hair reduction). FIG. 15*c* depicts the hand applicator from the application side, where the rectangular optic covers the printed circuit board mounted with multiple various selectable light sources 17, 17*a*. The size and form make it very suitable for hair reduction treatment where the radiation outlet can cover the whole area above the upper lip.

FIG. 16*a* illustrates an applicator, connected with a cable to the control mechanism, produced in the form of a quadrant tube, through which the blood to be treated passes and receives radiation from all four sides of the quadrant. FIG. 16*b* shows how the inner sides are equipped with printed circuit boards with light sources 17, 17*a* also containing transmitter coils, radiating pulse-shaped electromagnetic emission.

FIG. 16*c* illustrates the blood tube designed for inner radiation room in the applicator, through which the blood is passed during the treatment. The illustrated version is designed for the radiation of venous blood, for example in combination with infusions of light sensitive biopharmaceuticals (PDT therapy), but other applicator types are also available for use in artificial heart/lung machines (not illustrated).

Figure 17B:
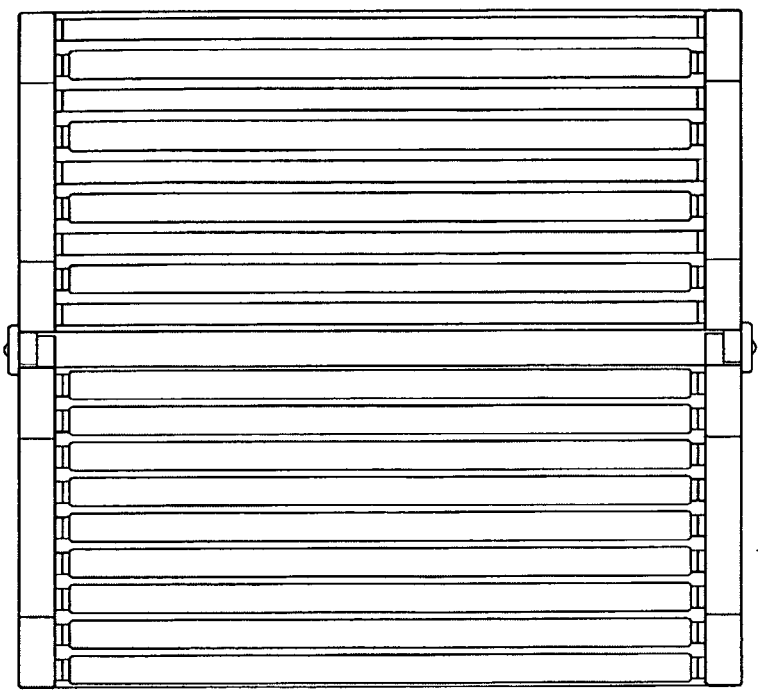
FIG. 17b shows the body applicator open, with the radiation surface of the lower and upper part.
Figure 17A:
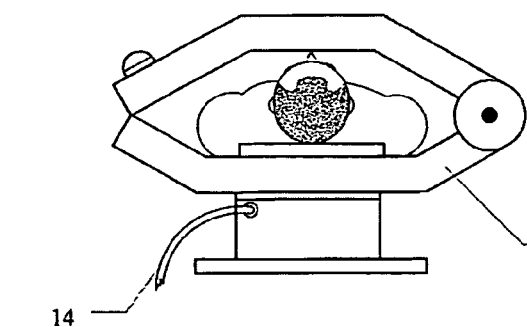
FIG. 17a shows the body applicator viewed from the end, in closed mode.

FIG. 17*a* shows a large body applicator connected with a cable to the control mechanism. The applicator is made of a lower and upper part hinged together and, in this illustration, shown closed, in an end view, ready for treatment.

FIG. 17*b* is an illustration where the applicator is opened and the radiation surface shows the light sources available for therapy. This model shows in the upper part every second light source as a standard UV light tube, and in between, the flattened oval tubes containing the light sources for the photodynamic therapy (PDT). The lower part is equipped only with the light tubes containing the light sources for the photodynamic therapy (PDT).

Figure 18A:
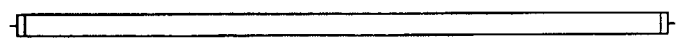
FIG. 18a illustrates a round light tube as seen from above.

FIG. 18*a* illustrates one version of an emitter for the body applicator, shaped like an ordinary round light tube of standard length, 2.15 meters, with a connector in each end for the supply.

Figure 18C:
FIG. 18c shows the light tube formed as a flat oval and viewed from above.
Figures 18B, 18D:
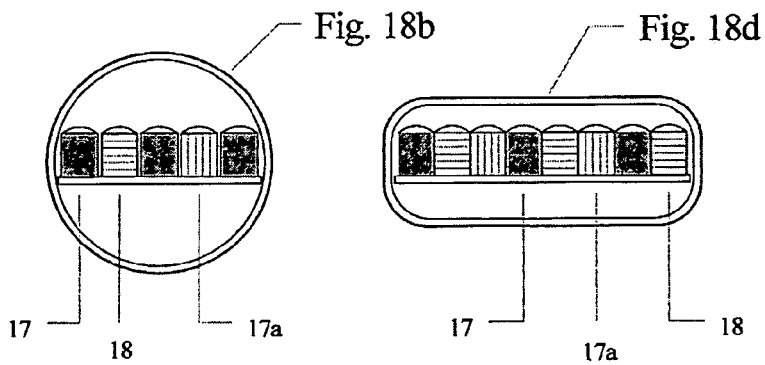
FIG. 18b illustrates the round light tube viewed from the end.
FIG. 18d shows the flat oval light tube viewed from the end.

FIG. 18*b* shows how the printed circuit board equipped with the light sources 17, 17*a* placed in the round tube.

FIG. 18*c* illustrates another version of an emitter for the body applicator, preferably formed as a flattened oval tube in a standard length of 2.15 meters and equipped with a standard connector in each end for the supply. FIG. 18*d* shows an end view of the tube with the printed circuit board equipped with light sources 17, 17*a*. The same printed circuit board can also contain a transmitter coil for the emission of pulse-shaped electromagnetic fields. The light tube is preferably mounted with a polarization 41 filter on the emitting side.

In the field of dermatology, light is used as a stand-alone therapy for wounds, leg ulcers, eczema, burns, etc., and as such is used to stimulate tissue directly. Light and the emission of pulse-shaped electromagnetic fields may also be used to treat tissue using photodynamic therapy (PDT) by activating chemical reactions in photosensitive chemicals introduced into or onto the tissue, such as photofrin, 5-aminolevulan acid, hematoporphyrin, verteporfin, chlorins, phthalodyanines, phenothiazine, and benzoporphyrin-derivative monoacid-A (A TMPn) etc. for healing solar keratoses, basal cell carcinoma, melanomas, etc.

PDT substances may be administered in various forms: lotion or cream for topical application, tablets or capsules for oral injection, and local injection of solutions or infusion.

Dimethylsulfoxide (DMSO) is a solution, which has the property of breaking down the barrier of the skin and is often used before administering PDT substances in order to increase the absorption thereof. Alternatively, PDT substances may be mixed with DMSO for application to the skin.

An instrument consisting of a handle with a head, wherein a number of needles are connected to a spring arrangement, can be used to pierce small, closely distanced holes in the upper layer of the skin before the PDT substances are applied, in order to increase and accelerate the absorption.

Treatment by light irradiation with the invented device should not commence until sufficient absorption by the target tissue is obtained. Simply waiting for empirically determined times to elapse can suffice, or photodynamic diagnostics (PD) may be employed to determine absorption. PD comprises viewing the target area under illumination of a particular spectral content (such as from a fluorescent light) and observing apparent colour change of the target tissue.

High-intensity treatments (higher doses of PDT substances and strong irradiation) are used where it is desired to destroy tissue, as in destroying tumor tissue to cure cancer, or in hair removal where it is desired to destroy the hair follicle. Low-intensity treatments are used where it is desired to energize affected cells and to stimulate the local immune system, as in the rehabilitation of epicondylitis, tendinitis, arthritis, arthroses, gout, and pulmonary diseases; or in the treatment of acne, actinic keratoses, warts, onychomycosis, psoriasis, dennatitis, and basal carcinoma; and in improving the appearance of wrinkles, cellulite, and fat deposits.

Low-intensity treatments have been observed to activate aspects of the local immune system such as the macrophages, which produce prostaglandin E2 (PGE2) and TNF (pro-inflammatory cytokines). There have also been observed an accumulation of leucocytes in the venules, and higher activity of the lymphocytes and plasma cells in the skin. The residual 5 content TNF-a of pro-inflammatory cytokines has been detected in the urine of patients after having PDT treatment.

Treatment with the invented device further enhances the efficacy of medicinal substances by photophoresis, a process of propelling fluids into the skin or tissue and propelling molecules through cell walls. The absorption process is accelerated, and the amount of PDT substance absorbed is increased. Other methods of phoresis are in use, such as galvanic iontophoresis, exchange phoresis, and phonophoresis. These methods create a concentration gradient across the skin, and a resultant Brownian molecular motion creates a thermal influence which enhances transfer of medicaments.

Photofrin is a PDT substance which is administered by injection, at a dosage of 1-2 mg. per kg. of the patient's weight. 48 hours is allowed for absorption of the photofrin by the tissue to be treated, during which time the patient is kept in dim light The treatment consists of irradiation by the invented device. The patient remains photosensitive for 6 to 8 weeks, and should avoid strong light and direct sunlight during that time.

ALA (5-Aminolavulinacid) is externally applied as a 10 to 20 percent mixture in an oil in water emulsion or in a cream. 4 to 6 hours is allowed for absorption, during which time the patient should remain in dim light. After treatment by irradiation from the invented device, the patient remains photosensitive for 24 to 48 hours, during which time he should avoid strong light and direct sunlight.

L-Phenylalanin is applied in liquid form as a lotion or a spray or in a cream form, in a 5 to 30 percent mixture according to the severity of the condition to be treated. Optical irradiation with the invented device may begin almost immediately. Alternatively, doses of 50 to 100 mg may be taken orally 30 to 60 minutes before irradiation. The patient is photosensitive for 24 hours after application.

PDT has been used successfully in the treatment of internal inoperable cancers. A biopharmaceutical (specifically, hematoporphyrin) is injected into the tumor tissue, and an optical method known as photodynamic diagnostics (PD) is used to determine when the biopharmaceutical has been absorbed by the entire tumor. Then the tumor tissue is irradiated with light typical for a dye laser, which activates the photosensitive reactors in the hematoporphyrin, whereby singlet oxygen is liberated. Singlet oxygen is toxic to protein and phosphor lipids in the tumor tissue, whereby the tumor is destroyed without destroying the surrounding tissue.

For treatment of skin keratosis (precancerous tissue), trials with, for example, 5-aminolevulinic acid have shown that it can be used effectively in PDT if introduced into oil in a water suspension which is then applied to skin keratosis and then irradiated with a light source. A fast and cosmetically perfect healing has been attained with a very low rate of recurrence compared to conventional treatments, such as cryotherapy.

Common dermatological conditions, such as acne, warts, onychomycosis (nail fungus) and wrinkles, can be successfully and effectively treated using PDT (with ALA/5-aminolevulanic acid) at a lower concentration than has conventionally been used. The treatment works not by causing cell death as light treatment has historically done, but instead works by stimulating the immune system so as to enable it to better control the inflammatory reaction to oil gland activity. The irradiation at multiple wavelengths as provided by the present invention enhances the efficacy of treatment in this manner.

Stimulating the immune system so as to reduce inflammatory reactions has also been found effective in the therapy of many other conditions, for example, epicondylitis (tennis elbow), tendinitis, gout, arthritis, arthroses, pulmonary diseases, and numerous other muscular and joint symptoms. Good results have been obtained with PDT in conjunction with the present invention's multiple wavelength output. Studies indicate that the patient often is pain-free after only one treatment, and the number of treatments can be reduced to 3-4, instead of 12-20 as required without the invented therapy.

The PDT substance is applied topically as cream or oil in water suspension, typically a 10-20 percent solution. Augmented action may be obtained by use of injection instead of or in addition to topical application. A large joint such as the knee requires 10-12 subcutaneous or intra-muscular injections, preferably at the trigger points, while for a smaller joint such as the elbow 5-6 injections is sufficient. First the trigger points are found and irradiated for 30 seconds with the hand applicator of the present invention. This gives an anaesthetic effect, which is useful for lessening discomfort from the injections. (Injection of the trigger points is a known method for pain reduction). Then, after determination that the PDT substance has been absorbed by the target tissue, the surface applicator of the present invention is folded around the target joint and irradiation takes place for 30 minutes.

Good results have also been obtained in physiotherapy and physical rehabilitation with the present invention's ability to radiate visible light together with several wavelengths of infrared light and pulse-shaped electromagnetic radiation which, in combination, give a much better effect in deep tissue affected by chronic disorders.

Thus, while the fundamental novel features of the invention have been shown and described in this prototypic application, it should be understood that various omissions and substitutions and changes in the form and details of the devices illustrated, and in their operation, may be made by those skilled in the art, without departing from the spirit of the invention. For example, it is expressly intended that all combinations of those elements and/or method-steps that perform substantially the same function in substantially the same way to achieve the same results are within the scope of the invention. Moreover, it should be recognized that structures and/or elements and/or procedures shown and/or described in connection with any disclosed form or embodiment of the invention may be incorporated in any other disclosed or described or suggested form or embodiment as a general matter of design choice. It is the intention, therefore, to be limited only as indicated by the scope of the claims appended hereto.

The invention is intended for medical/dental invasive treatment, physiotherapy/rehabilitation therapy, dermatological and cosmetic skin treatment.

What is claimed is:

1. A device for photodynamic therapy (PDT), treating tissue and electromagnetic field stimulation comprising:
   a stand;
   an adjustable machine applicator connected to the stand through a jointed arm, wherein the machine applicator contains a feedback sensor measuring at least one of any temperature changes in the tissue being treated and light reflected from the tissue being treated;
   a hand applicator connected to the stand by an electric circuit, the hand applicator being adapted for the application of light sensitive substances to human tissue, the tissue to be treated by at least one of air-pressure, iontophoresis and photophoresis;
   a control mechanism adjustable from a control panel for controlling at least one of the adjustable machine applicator and the hand applicator;
   at least one light source supported by at least one of the adjustable machine applicator and the hand applicator and including at least one of a semiconductor diode and a laser diode, the wavelength of the light source being adjustable;
   a light conductor supported by at least one of the adjustable machine applicator and the hand applicator;
   means for receiving light from at least one of the light sources;
   wherein the adjustable machine applicator comprises a scan engine for moving the at least one light source with linear movements;
   electromagnetic field transmitter coils supported by at least one of the adjustable machine applicator and the hand applicator, at least one of the frequency, length and amplitude of the electromagnetic field pulses being adjustable;
   a photo diagnostic system (PD) supported by at least one of the adjustable machine applicator and the hand applicator, and containing optics and a magnifier for photo diagnosis during the treatment; and
   a power unit for providing operating power to the control mechanism, wherein the at least one light source and the sensor are located on a printed circuit board.

2. A device according to claim 1, wherein the light source contains at least two diodes.

3. A device according to claim 2, wherein the two diodes emit light of different wavelengths.

4. A device according to claim 1, wherein the light sources are capable of being individually selected and switched ON or OFF.

5. A device according to claim 1, wherein the electromagnetic field transmitter coils are placed in the same printed circuit board on which the at least one light source is placed.

6. A device according to claim 1, wherein the stand is freely moveable on wheels.

7. A device according to claim 1, wherein the machine applicator comprises several single applicators hinged together so as to be adjustable at angles with respect to one another.

8. A device according to claim 1, wherein the machine applicator contains sensors connected to the control mechanism for measurement of reflected light for feedback control and automatic adjustment.

9. A device according to claim 1, wherein at least one of the at least one light sources is mounted to the adjustable machine applicator, and emits a fluorescent light for photo diagnosis.

10. A device according to claim 1, wherein the hand applicator contains at least one second light source connected to a pulse generator and at least one light outlet.

11. A device according to claim 10, wherein the at least one second light source comprises four selective light sources and a conductor for a light fiber cable.

12. A device according to claim 11, wherein the handpiece further comprises a circular printed circuit board with the four selective light sources, said four selective light sources comprising four different light sources, placed at 90° intervals;
   at least one light source emitting a fluorescent light for photo diagnosis; and
   a head comprising a light conductor rotable in four steps to selectively conduct light for photo diagnosis from the four different light sources to said at least one light outlet;
   wherein the circuit board is mounted behind the rotatable head.

13. A device according to claim 12, wherein a the light conductor includes a fibre optic cable suitable for dental use for directing light to a desired part of the body of the patient undergoing treatment.

14. A device according to claim 13, wherein the light conductor includes a flexible optic fibre cable for internal medical treatment.

15. A device according to claim 14, wherein at least one of the adjustable machine applicator and the hand applicator is formed as a rectangular tube containing additional printed circuit boards with light sources placed at all four inner walls for intensive radiation of a material which is located within the rectangular tube.

16. A device according to claim 14, wherein the machine applicator is adapted for whole body treatment and wherein the machine applicator is disposed for movement to a position above a bed on which a user undergoing treatment with the inventive device may lie.

17. A device according to claim 10, wherein the hand applicator is equipped with a shaft and a head and a printed circuit board equipped with semiconductor diodes.

18. A device according to claim 10, wherein the at least one light outlet is equipped with a lens and a polarization filter.

19. A device according to claim 10, wherein the at least one light outlet is equipped with at least one of a mounted lens and a polarization filter.

20. A device according to claim 1, wherein the hand applicator is formed as a rectangle with a handle at the upper part equipped with a start/stop switch.

21. A device according to claim 1, wherein at least one of the adjustable machine applicator and the hand applicator has a circular housing containing at least one of the at least one light source equipped with a lens.

22. A device according to claim 21, wherein the circular housing is equipped with a self-adhesive pad for placement on the patient's skin when radiating acupuncture points.

23. A device according to claim 1, further comprising:
a pressurized air-supply system connected by an air-supply tube to the hand applicator; and
a chamber integrated in the hand applicator containing the light-sensitive substances.

24. A device according to claim 23, wherein the air pressure is regulated and displayed on an instrument.

25. A device according to claim 23, wherein the air supply system provides air pulses to human tissue and wherein the length of the air pulses is regulated by means of a valve-system.

26. A device according to claim 25, wherein the valve system is mechanical.

27. A device according to claim 25, wherein the valve system is electrical.

28. A device according to claim 25, wherein the switch system is mechanical.

29. A device according to claim 25, wherein the switch system is electrical.

30. A device according to claim 25, wherein the hand applicator contains a switch system to activate the treatment.

31. A device according to claim 30, wherein the hand applicator contains a valve by the air inlet.

32. A device according to claim 31, where the hand applicator is exchangeable to suit the treatment area.

33. A device according to claim 32, where the hand applicator is equipped with a skin contact sensor system to protect from excessive treatment.

34. A device according to claim 33, wherein the hand applicator contains a valve-system which opens up automatically upon skin contact.

35. A device according to claim 34, wherein the chamber containing the light sensitive substances is integrated in the side of the hand applicator.

36. A device according to claim 35, wherein the hand applicator contains a dosage pump for the light-sensitive substances.

37. A device according to claim 36, where the hand applicator comprises a housing made of an insulating material, and a treatment head, said treatment head being made of a conducting material.

38. A device according to claim 37, where the hand applicator is connected to an iontophoresis generator in the control mechanism for use as an iontophoresis electrode.

39. A device according to claim 38, where the iontophoresis amplitude and frequency is capable of being regulated by the control mechanism.

40. A device according to claim 39, wherein the hand applicator contains at least one second light source connected to a pulse generator and at least one light outlet.

41. A device according to claim 40, wherein the hand applicator contains a second printed circuit board equipped with semiconductor diodes and a feedback sensor.

42. A device according to claim 1, wherein the means for receiving includes an optic lens.

43. A device according to claim 1, wherein the means for receiving includes a polarization filter.

44. The device according to claim 1, in which the printed circuit board is moved linearly.

45. The device according to claim 1, in which the printed circuit board is rotated.

46. A device according to claim 1, wherein the adjustable machine applicator comprises a radiation outlet, and the device further comprises a polarization filter covering the radiation outlet.

47. A method of treating tissue, comprising the steps of:
introducing a photosensitive substance to the tissue;
determining when the tissue has absorbed a predetermined level of the photosensitive substance; and
irradiating the tissue with a device according to claim 19.

48. A method according to claim 47, wherein the photosensitive substance is one of photofrin, 5aminolevulan acid, hematoporphyrin, verteporfin, chlorins, phthaldodyanines, phenothiazine, benzoporphyrin-derivative mono acid-A (A TMPn), L-Phenylalanin.

49. A method according to claim 47, wherein the step of determining when the tissue has absorbed a predetermined level of the photosensitive substance consists in observing that the tissue undergoes a predetermined colour change when viewed under a predetermined illumination.

50. A method according to claim 49, wherein the predetermined illumination consists of an optic system and a fluorescent light source.

* * * * *